United States Patent
Kawamoto (10) Patent No.: US 10,188,336 B2
(45) Date of Patent: Jan. 29, 2019

(54) PUNCTURE NEEDLE SENSOR MANUFACTURING METHOD

(71) Applicant: Terumo Kabushiki Kaisha, Shibuya-ku, Tokyo (JP)

(72) Inventor: Hideo Kawamoto, Tokyo (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 221 days.

(21) Appl. No.: 15/236,908

(22) Filed: Aug. 15, 2016

(65) Prior Publication Data

US 2016/0345883 A1   Dec. 1, 2016

Related U.S. Application Data

(60) Division of application No. 13/846,524, filed on Mar. 18, 2013, now Pat. No. 9,521,972, which is a (Continued)

(30) Foreign Application Priority Data

Sep. 30, 2010 (JP) ................. 2010-221867

(51) Int. Cl.
*H05K 3/00* (2006.01)
*A61B 5/157* (2006.01)
(Continued)

(52) U.S. Cl.
CPC ............ *A61B 5/157* (2013.01); *A61B 5/1411* (2013.01); *A61B 5/1473* (2013.01);
(Continued)

(58) Field of Classification Search
CPC . A61B 5/1411; A61B 5/1473; A61B 5/15003; A61B 5/150389;
(Continued)

(56) References Cited

U.S. PATENT DOCUMENTS 2,855,929 A * 10/1958 Hein, Jr. ................. A61M 5/32
604/411
4,672,734 A * 6/1987 Kawada ........... A61B 17/06004
163/1
(Continued)

FOREIGN PATENT DOCUMENTS

CN        1255639 C       5/2000
CN        1428533          7/2003
(Continued)

OTHER PUBLICATIONS

Office Action (First) dated Jun. 9, 2014, by the State Intellectual Property Office of the Peoples Republic of China in corresponding Chinese Patent Application No. 201180047575.3, and an English translation of the Office Action. (19 pgs).

(Continued)

*Primary Examiner* — Paul D Kim
(74) *Attorney, Agent, or Firm* — Buchanan Ingersoll & Rooney PC (57) ABSTRACT

A puncture needle sensor manufacturing method includes applying an insulation layer to a metal sheet and applying spaced apart stripe-shaped electrodes on the insulation layer after the insulation layer is applied on the metal sheet. The manufacturing method also includes cutting the metal sheet to produce a plate-shaped body that includes at least two of the electrodes. The plate-shaped body is press-worked to form the plate-shaped body into a tubular body, and a pointed, beveled end portion is formed at the distal end of the tubular body.

5 Claims, 7 Drawing Sheets

Related U.S. Application Data continuation of application No. PCT/JP2011/067324, filed on Jul. 28, 2011.

(51) Int. Cl.

| | | |
|---|---|---|
| *A61B 5/15* | (2006.01) | |
| *A61B 5/1473* | (2006.01) | |
| *A61B 5/153* | (2006.01) | |
| *A61B 5/145* | (2006.01) | |
| *A61B 5/1486* | (2006.01) | |
| *A61B 5/00* | (2006.01) | |

(52) U.S. Cl.
CPC ........ *A61B 5/1486* (2013.01); *A61B 5/14532* (2013.01); *A61B 5/14865* (2013.01); *A61B 5/15003* (2013.01); *A61B 5/153* (2013.01); *A61B 5/15087* (2013.01); *A61B 5/150282* (2013.01); *A61B 5/150389* (2013.01); *A61B 5/150396* (2013.01); *A61B 5/150511* (2013.01); *A61B 5/6848* (2013.01); *A61B 5/150847* (2013.01); *A61B 2562/12* (2013.01); *A61B 2562/125* (2013.01); *Y10T 29/49002* (2015.01)

(58) Field of Classification Search
CPC ........ A61B 5/150396; A61B 5/150847; A61B 5/15087; A61B 5/153; A61B 5/157; A61B 2562/12; A61B 5/150282; A61B 5/150511; A61B 5/14532; A61B 5/1486; A61B 5/6848

See application file for complete search history.

(56) References Cited

U.S. PATENT DOCUMENTS

| | | | | |
|---|---|---|---|---|
| 4,785,868 A | * | 11/1988 | Koenig, Jr. | ............ A61M 5/32 163/5 |
| 5,951,528 A | * | 9/1999 | Parkin | .................. A61M 5/329 600/4 |
| 6,883,552 B2 | | 4/2005 | Ooyauchi et al. | |
| 7,637,135 B2 | * | 12/2009 | Homig | .................. B21C 37/065 72/367.1 |
| 2003/0127149 A1 | | 7/2003 | Ooyauchi et al. | |
| 2005/0126241 A1 | | 6/2005 | Ooyauchi et al. | |
| 2008/0255440 A1 | * | 10/2008 | Eilersen | ............. A61B 5/14532 600/373 |
| 2009/0043227 A1 | | 2/2009 | Fujiwara et al. | |
| 2016/0136357 A1 | * | 5/2016 | Yang | ................... A61M 5/1723 604/66 |

FOREIGN PATENT DOCUMENTS

| | | | |
|---|---|---|---|
| CN | 101132733 | A | 2/2008 |
| CN | 101374458 | A | 2/2009 |
| JP | 9-94231 | A | 4/1997 |
| JP | 2007-14381 | A | 1/2007 |
| JP | 2007-14382 | A | 1/2007 |
| JP | 2007-54407 | A | 3/2007 |
| JP | 3943390 | B2 | 4/2007 |

OTHER PUBLICATIONS

Office Action (Second) dated Nov. 18, 2014, by the State Intellectual Property Office of the Peoples Republic of China in corresponding Chinese Patent Application No. 201180047575.3, and an English translation of the Office Action. (11 pgs).

Office Action (Notice of Reasons of Rejection) dated Nov. 28, 2014, by the Japanese Patent Office in corresponding Japanese Patent Application No. 2010-221867 and an English translation of the Office Action. (5 pgs).

Office Action (Notice of Reasons of Rejection) dated Jun. 4, 2014, by the Japanese Patent Office in corresponding Japanese Patent Application No. 2010-221867 and an English translation of the Office Action. (7 pgs).

International Search Report dated Aug. 30, 2011 by the Japanese Patent Office in International Application No. PCT/JP2011/067324, and English translation (4 pgs).

\* cited by examiner

PUNCTURE NEEDLE SENSOR MANUFACTURING METHOD

This application is a divisional of Ser. No. 13/846,524 filed on Mar. 18, 2013, now U.S. Pat. No. 9,521,972, which is a continuation of International Application No. PCT/JP2011/067324 filed on Jul. 28, 2011, which claims priority to Japanese Patent Application JP2010-221867 filed on Sep. 30, 2010, the entire content of both of which is incorporated herein by reference.

TECHNICAL FIELD

The present invention generally pertains to a tubular sensor for detecting a constituent in a liquid such as body fluid, a method of manufacturing such a sensor, and a constituent measuring device using the tubular sensor.

BACKGROUND DISCUSSION

Conventionally, for measurement of various constituents in body fluid, a method has been adopted in which measurement is conducted by use of specific enzymatic substances capable of reacting with specific constituents in the body fluid. Especially, measurement of blood glucose level is important for monitoring a patient's condition. Therefore, self-monitoring of blood glucose is recommended in which daily variation in blood glucose level is monitored by the patient himself or herself.

In the measurement, it is necessary, for example, for the patient to puncture the skin of the patient's finger or the like with a puncturing device having a puncture needle, to press the surroundings of the punctured part with a finger or the like to squeeze out blood, and to take the squeezed-out blood into a disposable sensor mounted to a measuring device. Therefore, this approach has had a problem as to workability.

To help ease the complicated nature of this measurement effort, a device has been proposed in recent years in which a sensor and a puncture needle are integrated.

For instance, Japanese Patent Laid-open No. 2007-54407 describes two electrodes arranged in a tubular puncture needle in which a cavity exists. The electrodes in the puncture needle are connected to a control substrate through electric wires, and measurement of a current is conducted.

In this method, the blood glucose level can be measured by using the blood sampled into the puncture needle. Therefore, the amount of blood needed for measurement can be reduced. In addition, after the patient's skin is punctured with the puncture needle, the measurement can be performed directly in that condition. This makes it possible to alleviate the burden on the patient.

Japanese Patent Laid-open No. Hei 9-94231 describes that an oxygen fixation working electrode, a counter electrode and a reference electrode are arranged in a capillary tube connected to a minute injection needle. In this method, blood is guided into the capillary tube through the minute injection needle by capillarity, and an oxidation current is measured by the three electrodes in the capillary tube.

On the other hand, a method of manufacturing a tubular body having a cavity therein along its longitudinal direction, such as an injection needle, is proposed in Japanese Patent No. 3943390. In this method, first a thin metal sheet is blanked into a development shape of the desired tubular body. Then, the thin sheet in the development shape of the tubular body is gradually rounded by press working, to mold it into a tubular shape.

In the technique described in Japanese Patent Laid-open No. 2007-54407, however, it is necessary, after separate production of a puncture needle and electrodes, to immobilize the electrodes in a minute space inside the puncture needle. Thus, this technique has problems in regard of immobilization accuracy and productivity.

In addition, for accurate detection of a current generated by an enzymatic reaction, it is desirable to keep the distance between the two electrodes constant. When there is unevenness in the immobilization accuracy of the electrodes as above-mentioned, however, dispersion in the inter-electrode distance is generated, making it impossible to perform a highly accurate constituent detection.

The technique described in Japanese Patent Laid-open No. Hei 9-94231 requires insertion of a working electrode, a counter electrode and a reference electrode which are formed in a small-diameter rod-like shape have into a capillary tube. Since the three electrodes are immobilized in the cavity of the capillary tube, it is difficult to arrange the electrodes with high positional accuracy. Therefore, dispersion in inter-electrode distance is liable to be generated, possibly influencing the constituent detection accuracy.

In addition, two members consisting of the puncture needle and the capillary tube are needed, and a step of connecting them together is also needed, leading to a rise in manufacturing cost.

SUMMARY OF INVENTION

According to one aspect, a tubular sensor comprises: a tubular body having a cavity extending through the tubular body in a longitudinal direction of the tubular body, the tubular body possessing an inner wall surface; an insulation layer on the inner wall surface of the tubular body; and a plurality of electrodes on the insulation layer and extending in the longitudinal direction of the tubular body, each of the plurality of electrodes extending continuously from one end of the tubular body to an opposite end of the tubular body. The tubular sensor is configured to perform highly accurate constituent detection and can be manufactured relatively easily.

According to another aspect, tubular sensor comprising a tubular body possessing a distal end portion terminating at a distal-most end, a proximal end portion terminating at a proximal-most end, and a cavity extending throughout the tubular body which opens at both the distal-most end and the proximal-most end of the tubular body, with the tubular body possessing an inner wall surface facing towards and surrounding the cavity, and wherein the distal end portion of the tubular body being beveled and pointed to puncture a patient's skin so that a blood sample from the patient's body enters the cavity at the distal end portion of the tubular body. The tubular sensor also comprises an insulation layer fixed on the tubular body and directly in contact with the inner wall surface of the tubular body, wherein the insulation layer is made of an insulating material which is different from material forming the tubular body, the insulating layer possessing an inner surface, and a plurality of separate and circumferentially spaced apart electrodes fixed on the tubular body and directly in contact with the inner surface of the insulation layer. Each of the plurality of electrodes is electrically conductive and extending continuously from adjacent the distal end portion of the tubular body towards the proximal end of the tubular body, with the electrodes projecting inwardly toward the cavity relative to portions of the inner wall surface between the electrodes, and with the portions of the inner surface of the insulation layer between the electrodes being exposed to the cavity so that blood entering the cavity at the distal end portion of the tubular body contacts the portions of the inner surface of the insulation layer between the electrodes.

The electrodes are formed over the inner wall surface of the tubular body, with the insulation layer between the inner wall surface of the tubular body and the insulation payer, and so the electrodes are immobilized onto the tubular body and an inter-electrode distance can be easily kept relatively constant.

According to another aspect, a constituent measuring device includes the tubular sensor described above, a measuring unit configured to measure an electrical signal outputted by the tubular sensor; and a control unit configured to compute a detection signal obtained upon measurement at the measuring unit and to determine a value of a constituent in a liquid sampled into the tubular sensor.

The constituent measuring device is configured by use of the above-mentioned tubular sensor. Therefore, the electrodes are immobilized onto the tubular body, so that the inter-electrode distance is kept relatively constant. As a result, an electrical signal according to the constituent of the liquid sampled into the tubular sensor can be detected with high accuracy.

Another aspect of the disclosure here involves a tubular sensor manufacturing method. The method includes forming an insulation layer on a thin metal sheet, and forming a plurality of electrodes on the insulation layer in stripes. In addition, the method involves cutting the thin metal sheet formed with the insulation layer and the electrodes to form a plate-shaped body in a developmental shape of a tubular body having a longitudinally extending cavity, and press working the plate-shaped body to form the tubular body.

According to the tubular sensor manufacturing method disclosed here, it is possible to rather easily produce the tubular body with the electrodes immobilized on the inner wall surface. Therefore, it is possible to omit a process of separately producing a tubular body and electrodes, and thereafter inserting the electrodes into the tubular body and immobilizing the electrodes in the tubular body.

In addition, since the electrodes can be formed in the state of being immobilized over the inner wall surface of the tubular body, the inter-electrode distance can be kept constant.

The immobilization of the electrodes on the inner wall surface of the tubular body so that the inter-electrode distance is kept constant allows accurate current detection to be achieved.

In addition, with the constituent measuring device at issue here, the above-mentioned tubular sensor is used, and so the electrical signal according to the constituent of the liquid sampled into the tubular sensor can be detected with high accuracy.

Because the sensor manufacturing method no longer requires separately producing the tubular body and electrodes, inserting the electrodes into the tubular body, and then immobilizing the electrodes in the tubular body, the manufacturing steps can be simplified, and a reduction in cost can be realized

BRIEF DESCRIPTION OF DRAWINGS

The foregoing and additional details and aspects of the tubular sensor, manufacturing method and constituent measuring device will become more apparent from the detailed description below considered with reference to the accompanying drawing figures which are briefly described below.

DETAILED DESCRIPTION

Examples of the tubular sensor, the constituent measuring device and the manufacturing method are described in more detail below, though it is to be understood that the invention here is not limited to the examples described and illustrated. The following detailed description is made in the following order.
1. First Embodiment
1-1. Tubular Sensor
1-2. Tubular Sensor Manufacturing Method
2. Second Embodiment
2-1. Constituent Measuring Device
1. First Embodiment
1-1. Tubular Sensor Referring to FIGS. 1A-1C, the tubular sensor 100 according to this embodiment includes a tubular body 1 having a longitudinally extending internal cavity, an insulation layer 2 on the inner wall surface of the tubular body 1, and electrodes 3 on the insulation layer 2. In the illustrated embodiment, the insulation layer 2 is in direct contact with the inner wall surface of the tubular body 1, and the electrodes 3 are in direct contact with the insulation layer 2. In the illustrated embodiment, the insulation layer 2 covers the entirety of the inner wall surface of the tubular body 1.

Figure 1A:
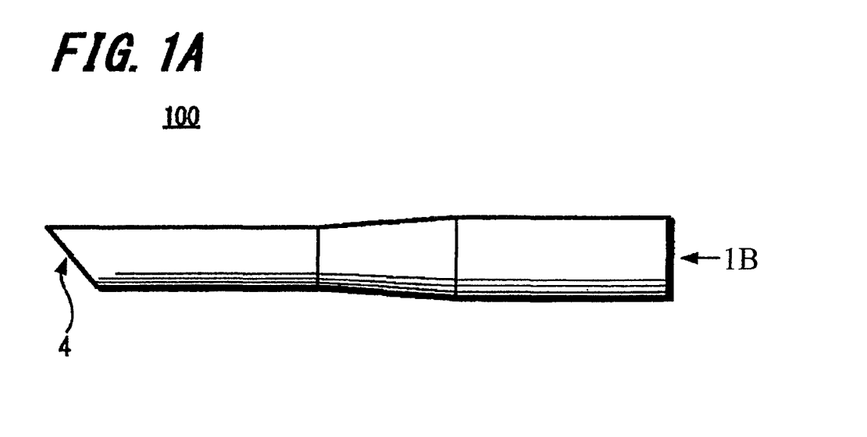
FIG. 1A is a side view of a tubular sensor according to a first embodiment disclosed here by way of example.
Figure 1B:
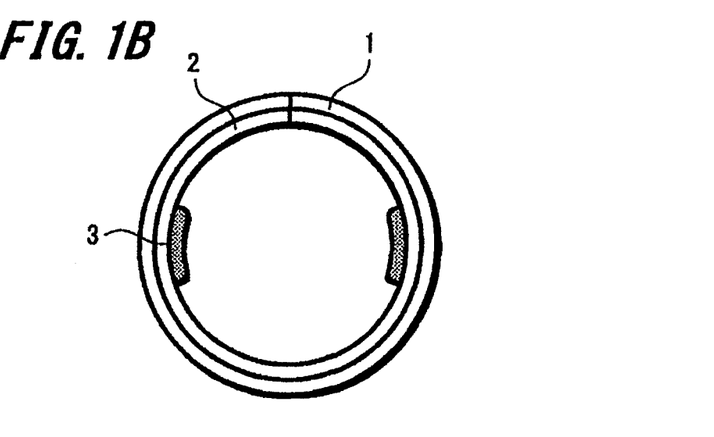
FIG. 1B is an illustration of the tubular sensor as viewed in a longitudinal direction of the tubular sensor in the direction of the arrow 1B.
Figure 1C:
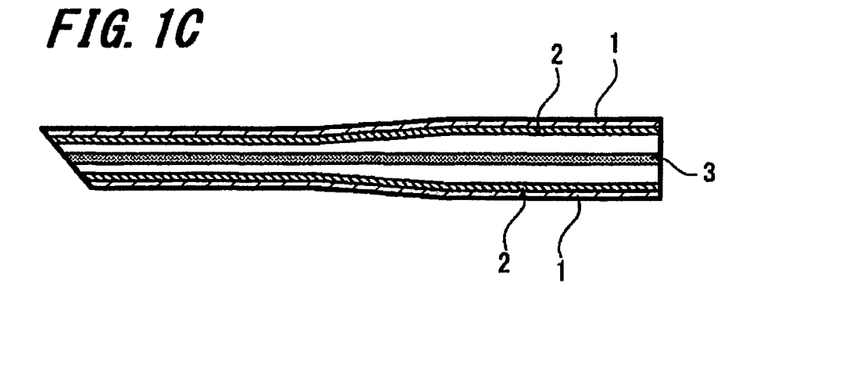
FIG. 1C is a longitudinal cross-sectional view of the tubular sensor according.

The tubular body 1 is formed, for example, of a metallic material. Examples of the metallic material include stainless steels such as SUS304, SUS316, etc., aluminum, aluminum alloys, and titanium. Other materials may also be used insofar as they are comparable to the just-mentioned metallic materials in hardness, ductility and plasticity.

The tubular body 1 has a hollow structure in which a cavity extends throughout in the longitudinal direction of the body. The tubular body 1 in this example is shaped to possess different outside diameters and different inside diameters at both ends of the tubular body.

In addition, the outside diameter and inside diameter of the tubular body 1 are not limited to specific dimensions. In a case where the tubular body 1 is to be used as a puncture needle, the outside diameter of the tubular body 1 is, for example, 0.1 to 0.3 mm.

The length of the tubular body 1 is also not particularly limited. In the case of use as a puncture needle, however, the length is appropriately selected according to the puncture depth and strength required.

In the case where the tubular body 1 is to be used as a puncture needle, it may be formed with a cutting edge surface 4 at one end of the tubular body.

The insulation layer 2 is provided on the inner wall surface of the tubular body 1. The insulation layer 2 is formed, for example, of an insulating plastic material. The plastic material is selected, for example, from a group consisting of polyvinyl chloride, polycarbonates, polysulfones, nylons, polyurethane, polyesters, acrylic resins, polystyrene and the like. Also usable are other non-conductive materials than plastic materials, such as cellulose.

In addition, the insulation layer 2 can be formed by various methods such as adhesion, welding, coating, printing, and semiconductor process.

The electrodes are on the insulation layer 2 and extend in the longitudinal direction of the tubular body 1 continuously from one end to the other end of the tubular body 1. As will be described later, the electrodes 3 can be formed by printing, coating or the like while using an Ag paste, a carbon paste or the like. Other materials may also be used insofar as they have conductivity suitable for use as electrodes, and the electrodes 3 may be formed by other semiconductor processes such as vapor deposition and sputtering.

In addition, the number of electrodes 3 in this embodiment is at least two. FIG. 1B illustrates an example in which two electrodes 3 are arranged. In a case of measurement of blood glucose level, for example, the two electrodes 3 are used as a working electrode and a counter electrode, respectively. In a case where three or more electrodes 3 are formed, two of the electrodes are selected to be used as a working electrode and a counter electrode, respectively.

Where three or more electrodes 3 are provided, as will be described later, there is a merit that even when troubles occur with one of the electrodes 3 in the manufacturing process, two electrodes selected from among the remaining electrodes can be used as a working electrode and a counter electrode, respectively.

On the electrodes 3, a reagent containing an enzyme such as glucose oxidase and glucose dehydrogenase is immobilized in a dry state. Glucose in blood sampled into the cavity of the tubular body 1 is oxidized by the enzyme, and a current arising from transfer of electrons through a mediator is detected by the electrodes 3.

Figure 2:
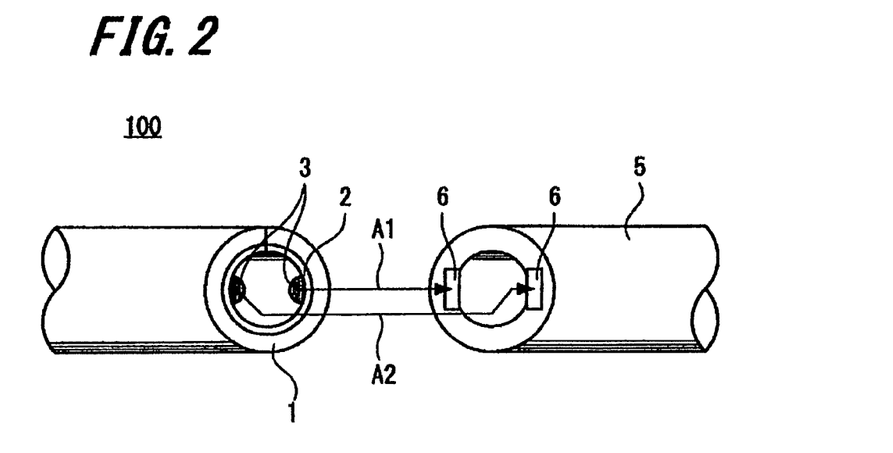
FIG. 2 is an illustration of a manner in which the tubular sensor shown in FIGS. 1A-1C is connected to an external apparatus.

FIG. 2 shows the electrodes 3 connected to terminals 6 of a connection section 5 of, for example, a measuring instrument for measurement of this current. The terminals 6 are formed, for example, from a conductive rubber such as Zebra rubber. In addition, as indicated by arrows A1 and A2, the electrodes 3 of the tubular sensor 100 and the terminals 6 are made to correspond to each other and are connected to each other with positional adjustment. That is, the electrodes 3 and the terminals 6 are first aligned. In this state, the electrodes 3 and the terminals 6 are connected to each other. The tubular body 1 and the connection section 5 are connected, with the electrodes 3 and the terminals 6 adjacent to each other.

The terminals 6 may be formed from material other than the above-mentioned material. The configuration of the connection, such as the shape, is not specifically limited.

In the case of measurement of blood glucose level, for example, the tubular sensor 100 (see FIG. 10) is configured to puncture a patient's skin. Then, blood sampling may be carried out, with the tubular sensor 100 maintained in a punctured state with respect to the patient's skin. Alternatively, after the tubular sensor 100 is pulled out, the blood exuding onto or flowing to the skin surface may be sampled. The blood is sampled into the cavity of the tubular body 1 by, for example, capillary action.

Thus, in the tubular sensor 100 according to this embodiment, the electrodes 3 are immobilized on the inner wall surface of the tubular body 1 having the longitudinally extending cavity. This helps ensure that it is relatively easy to keep the inter-electrode distance between the working electrode and the counter electrode constant, and enhanced accuracy of measurement can be achieved.

In addition, as the electrodes 3, there can be used electrodes which are formed by a semiconductor process, for example. This helps ensure that the tubular sensor 100 can be manufactured collectively or integrally as will be described later. Accordingly, there is no need to insert electrodes into a cavity of a tubular body or to adhere the electrodes to the tubular body, after separately forming the tubular body and the electrodes. As a result, manufacturing steps can be simplified, and productivity can be enhanced.

In the case where the tubular sensor 100 is provided with the cutting edge surface 4, it is possible, after puncture of a patient's skin by the tubular sensor 100, to sample blood under that condition and to measure the blood glucose level or the like. Therefore, the amount of work can be reduced, and the burden on the patient can be alleviated accordingly. In addition, according to the present embodiment, the electrodes 3 are disposed in the cavity of the tubular body 1. Therefore, the measurement can be performed with a relatively small amount of blood sampled into the cavity.

Figure 3A:
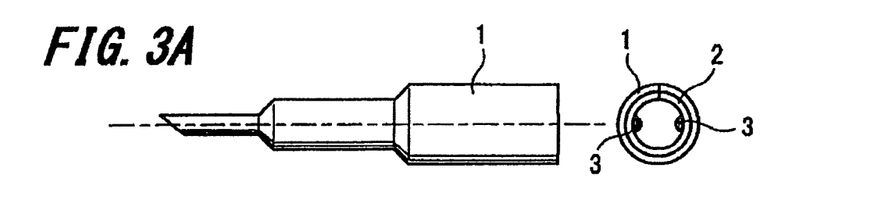
FIG. 3A is an illustration of a tubular sensor in which outside diameter and inside diameter are varied stepwise.
Figure 3B:
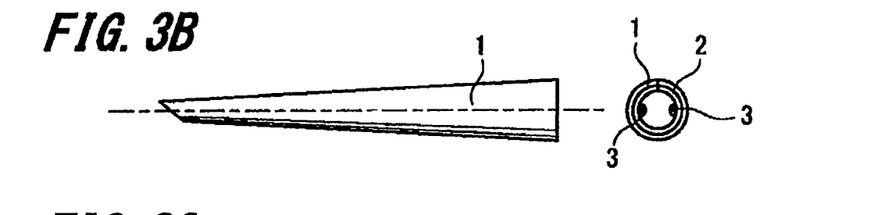
FIG. 3B is an illustration of a tubular sensor in which outside diameter and inside diameter are varied continuously.
Figure 3C:
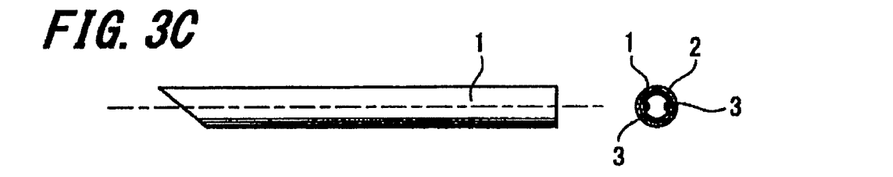
FIG. 3C is an illustration of a tubular sensor in which outside diameter and inside diameter are constant.

As mentioned above, this embodiment, representing one example of the disclosure here, has a shape in which the outside diameter of the tubular body 1 has different values (dimensions) at both ends of the tubular body 1. The shape, however, may be such that the outside diameter varies in three steps as shown in FIG. 3A, or may be such that the diameter varies continuously from the distal end to the proximal end as shown in FIG. 3B. Further, the shape may be such that the outside diameter is constant as shown in FIG. 3C.

In addition, the cross-sectional shape of the tubular body 1 is not restricted to a true circle but may be a polygon, such as a tetragon and a hexagon, or may be an ellipse.

1-2. Tubular Sensor Manufacturing Method

A method of manufacturing the tubular sensor 100 according to this embodiment will be described below, referring to FIGS. 4 to 9. Parts corresponding to those in FIG. 1 are denoted by the same reference numerals as used in FIG. 1.

Figure 4A:
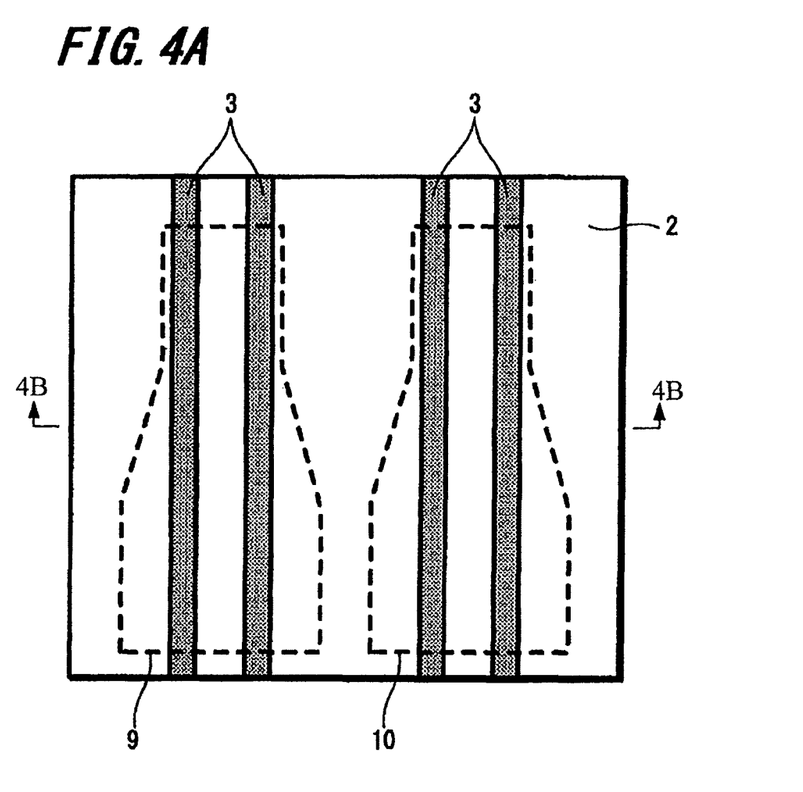
FIG. 4A is a top plan view of a thin metal sheet formed with an insulation layer and electrodes, as viewed from above.
Figure 4B:
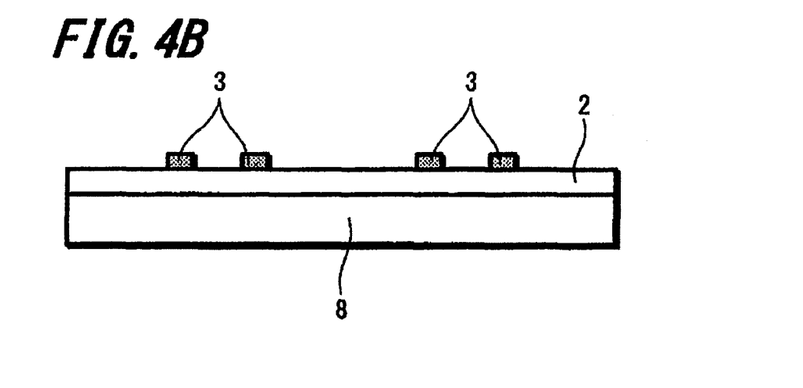
FIG. 4B is a cross-sectional view of the thin metal sheet formed with the insulation layer and electrodes taken along the section line 4B-4B.

FIG. 4 is a top plan view showing a condition where the insulation layer 2 and the electrodes 3 are respectively formed over or on a relatively thin metal sheet 8, and FIG. 4B is a cross-sectional view taken along the section line 4A-4A of FIG. 4A.

The relatively thin metal sheet 8 is formed, for example, of a metallic material. Examples of the metallic material include stainless steels such as SUS304, SUS316, etc., aluminum, aluminum alloys, titanium, and titanium. Other materials may also be used insofar as they are comparable to the just-mentioned materials in hardness, ductility and plasticity.

The method involves first forming the insulation layer 2 on the relatively thin metal sheet 8. The insulation layer 2 is formed, for example, from an insulating plastic material. The plastic material is selected, for example, from a group consisting of polyvinyl chloride, polycarbonates, polysulfones, nylons, polyurethane, polyesters, acrylic resins, and polystyrene. Also usable are other non-conductive materials than plastics, such as cellulose.

In the case where the insulation layer 2 is formed from an organic polymer material such as just-mentioned, the insulation layer 2 can be formed, for example, by a coating method such as spin coating, or by a printing method such as screen printing. The insulation layer 2 may be formed by other methods such as semiconductor processes, and adhesion or welding or the like techniques.

After the insulation layer 2 is formed on the relatively thin metal sheet 8, the electrodes 3 are formed in stripes, for example. The electrodes 3 are formed, for example, from Ag, carbon or the like. Other metals, alloys and conductive organic materials may also be used insofar as they have ductility and plasticity such that they can endure the subsequent press working.

Formation of the electrodes 3 can be conducted by a printing method using an Ag paste, a carbon paste or a solution containing other conductive substance.

In addition, in a case where the electrodes 3 are formed from a conductive inorganic material, a process may be employed in which a conductive film is formed by such a method as sputtering, vapor deposition or plating, and thereafter the conductive film is patterned by etching, lift-off or the like to form the electrodes 3.

Thus, in this embodiment, the electrodes 3 are preliminarily formed by a semiconductor process, in carrying out the manufacturing process. Therefore, unlike in the conventional process, there is no need to separately produce a puncture needle and electrodes, to insert the electrodes into the puncture needle, and to adhere the electrodes onto the puncture needle. Consequently, integral manufacturing in which the needle and the electrodes are formed together as a single unitary structure through a series of processes is possible.

After the electrodes 3 are formed, appropriate shapes as if obtained by unfolding desired tubular bodies 1 are cut, as indicated by broken lines 9 and 10 in FIG. 4A, to form plate-shaped bodies. That is, to form a tubular body of desired shape or configuration, the metal sheet with the electrodes applied is cut into a shape that is the same as the shape which would result if the tubular body of the desired shape or configuration was unfolded along its longitudinal extent. The cutting may be mechanical cutting by use of a press, or may be heat-aided cutting such as laser cutting.

Figure 10:
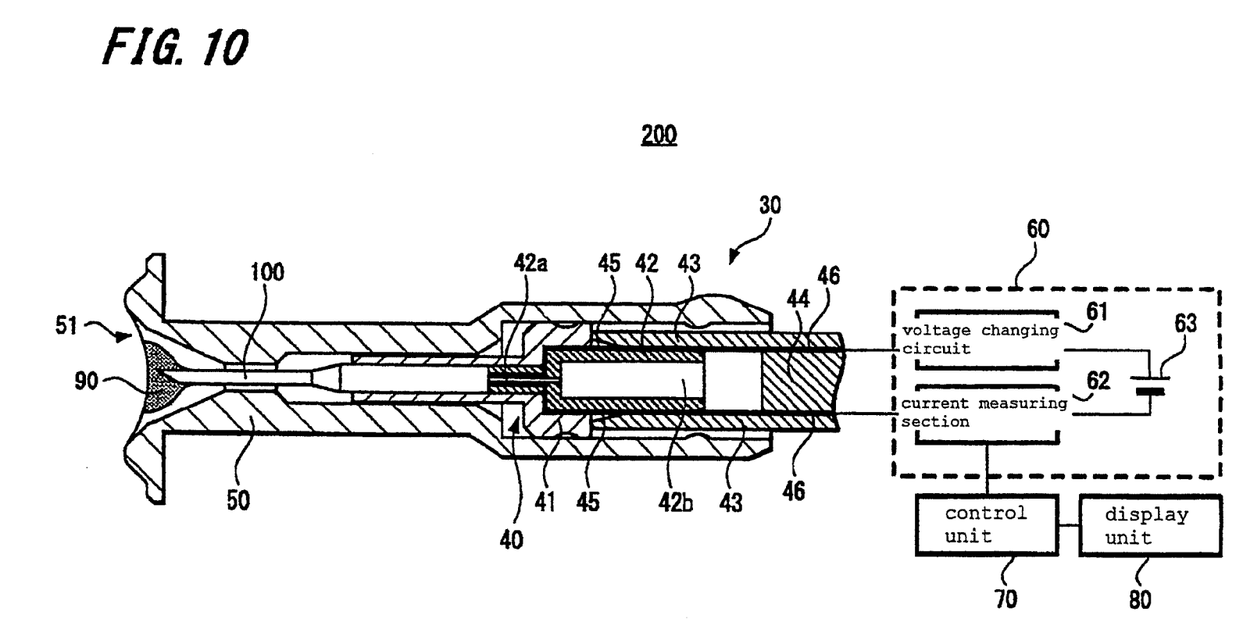
FIG. 10 is an illustration of a constituent measuring device according to a second embodiment disclosed here as another example.

In addition, here, the cutting is conducted through position adjustment such that two electrodes 3 are included in each of the development shapes indicated by the broken lines 9 and 10. The term "development shape" refers to the shape or configuration of the plate-shaped body which, when subsequently processed (for example, by press-working), produces the shape of the desired product. For example, in connection with the production of tubular sensor 100 forming a puncture needle as shown in FIG. 10, the development shape is the shape which will produce the tubular sensor 100 when the developmental shape is subsequently processed.

Figure 5A:
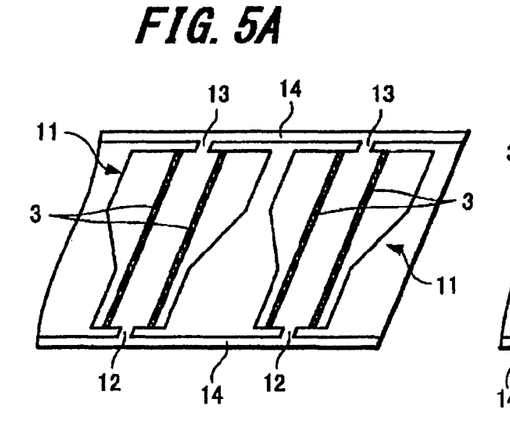
FIG. 5A is an illustration of a plate-shaped body formed by cutting a thin metal sheet.

FIG. 5A shows the state after the cutting. As a result of the cutting, plate-shaped bodies 11 having the development shapes of the desired tubular bodies 1 are formed. A plate-shaped body 11 is thus formed. This plate-shaped body 11 remains connected to surrounding frame parts 14 of the thin metal sheet through connection parts 12, 13.

In addition, the connection parts 12, 13 are provided at the longitudinally spaced apart ends of the plate-shaped body 11, i.e., on the oppositely disposed ends of the tubular body formed when the plate-shaped body 11 is molded into the tubular body 1.

Figure 5B:
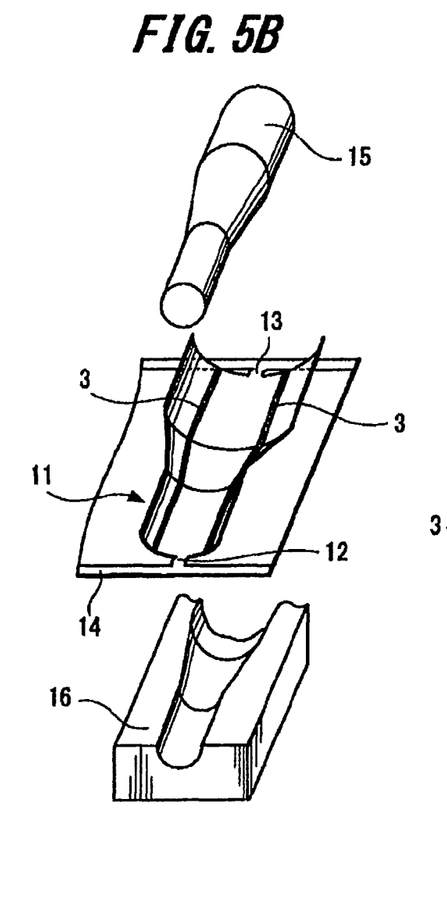
FIG. 5B is an illustration of a manner in which the plate-shaped body is press worked by use of an upper die and a lower die.

Next, as shown in FIG. 5B, the plate-shaped body 11 is press worked from upper and lower sides by use of an upper die 15 and a lower die 16, whereby the plate-shaped body 11 is gradually rounded through curving.

For instance, a projected die is used as the upper die 15 disposed on the upper side of the plate-shaped body 11, whereas a recessed die is used as the lower die 16 disposed on the lower side of the plate-shaped body 11.

Figure 6:
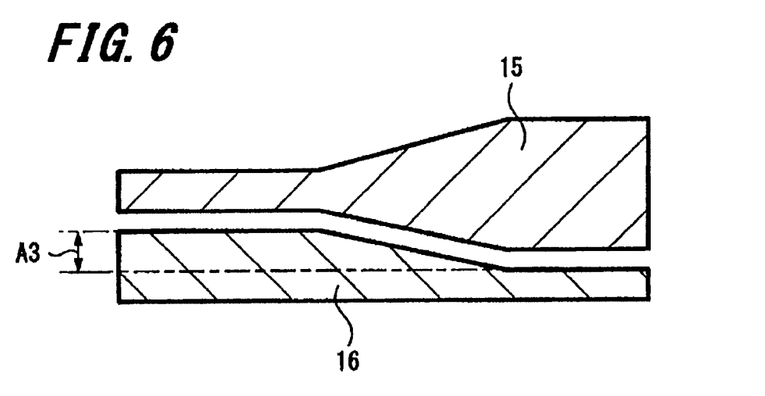
FIG. 6 is a schematic cross-sectional view of the upper die and the lower die for use in press working of the plate-shaped body.

FIG. 6 is a cross-sectional view of the upper die 15 and the lower die 16. The lower die 16 has a shape provided with a step, as indicated by A3. Accordingly, the press working is conducted while an end portion on a smaller diameter side of the tubular body to be formed is lifted up and displaced upward in relation to the frame part 14.

This helps ensure that, even in the case of the tubular body having different diameters at both ends, an axis of the tubular body and the frame part 14 can be maintained parallel to each other. In this case, the axis of the tubular body is located above the thin metal sheet surface of the frame part 14.

Figure 5C:
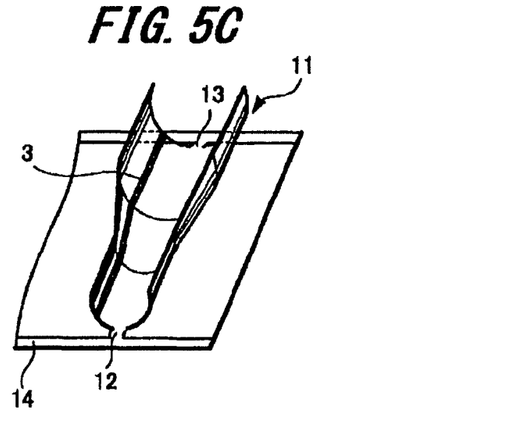
FIG. 5C is an illustration of a condition in which the plate-shaped body is curved by press working.

Returning to FIG. 5, as the press working is repeated gradually, the plate-shaped body 11 is curved into a U-shaped form as shown in FIG. 5C. In this process, the plate-shaped body 11 may be gradually curved by changing the sizes of the upper die 15 and the lower die 16, or may be curved while using the same upper and lower dies.

Figure 5D:
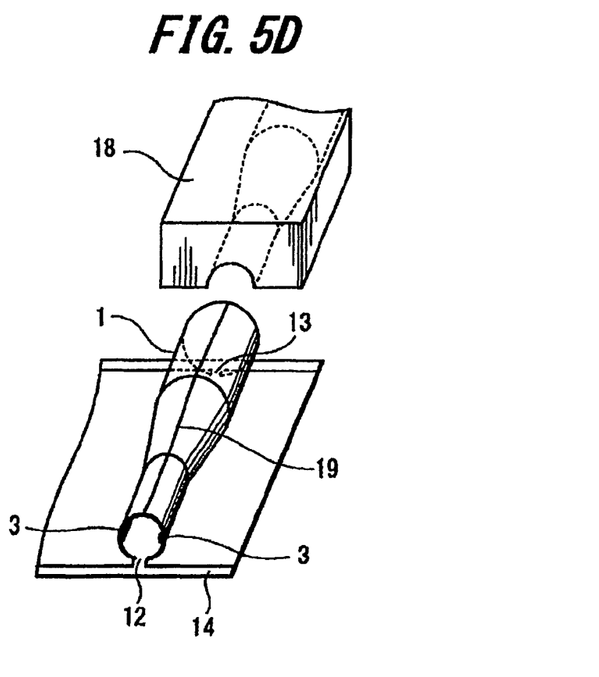
FIG. 5D is an illustration of a manner in which the plate-shaped body is worked into a closed curved surface by use of another upper die to form a tubular body.

After the curving of the plate-shaped body 11 proceeds to the condition of FIG. 5C, pressing is conducted this time by use of a recessed upper die 18, as shown in FIG. 5D, and the plate-shaped body 11 is further curved into a closed curved surface. As a result, the tubular body 1 is formed.

In a case where a seam 19 in the tubular body 1 can be made liquid-tight by only the press working, cutting of the connection parts 12, 13 results in the tubular body 1 being cut off from the frame parts 14. The seam 19 of the plate-shaped body 11 may be joined to be liquid-tight by use of an adhesive or by welding or the like.

It is to be noted here, however, that joining by welding is preferably employed, since the tubular body 1 is formed from a metal and has a very small outside diameter. The welding method is not limited to a specific welding method. For instance, welding can be conducted employing carbon dioxide gas laser, YAG laser, excimer laser or the like.

With the tubular body 1 cut off from the frame parts 14, the tubular sensor 100 (see FIG. 1) in this embodiment is substantially completed. In the case of using the tubular sensor 100 as a puncture needle, the cutting edge surface 4 (see FIG. 1) is formed, for example, by subjecting a distal end of the tubular body 1 to cutting, grinding, and polishing or the like. The distal end portion of the tubular body is beveled and configured to puncture skin of a patient and so a sharp pointed beveled end is formed on the tubular body 1 to produce a puncture needle.

In the case of using the tubular sensor 100 as a sensor for measurement of blood glucose level or the like, a reagent containing an oxidoreductase is applied onto the electrodes 3 before cutting-out of the plate-shaped body 11. Or, alternatively, a process may be adopted in which the tubular body 1 is formed and cut off from the frame parts 14, and thereafter the distal end of the tubular body 1 is immersed in a liquid reagent to deposit the reagent on the electrodes 3.

While an example in which two electrodes are arranged in the tubular body has been described here, three or more electrodes may be arranged. In that case, the method is carried out to arrange the electrodes 3 and perform the cutting so that three electrodes are included in the plate-shaped body.

Figure 7A:
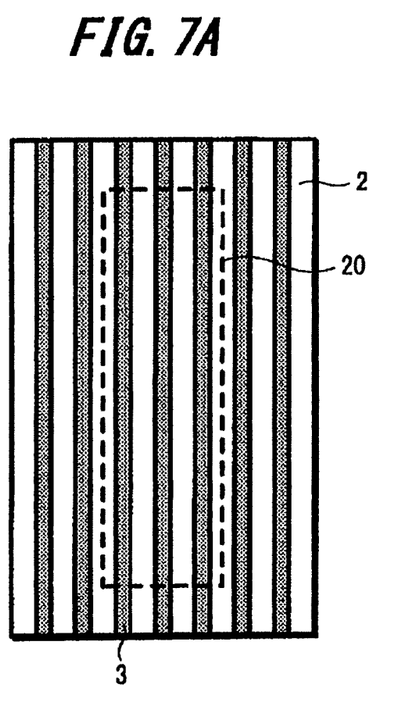
FIG. 7A is an illustration of electrodes arranged in a plate-shaped body to be molded into a tubular body having a constant diameter.

For instance, in the case of forming a tubular body with an outside diameter that is constant along the longitudinal extent of the tubular body, it suffices to conduct the cutting so that three electrodes 3 are included in the plate-shaped body in the development shape as indicated by broken line 20 in FIG. 7A.

Figure 7B:
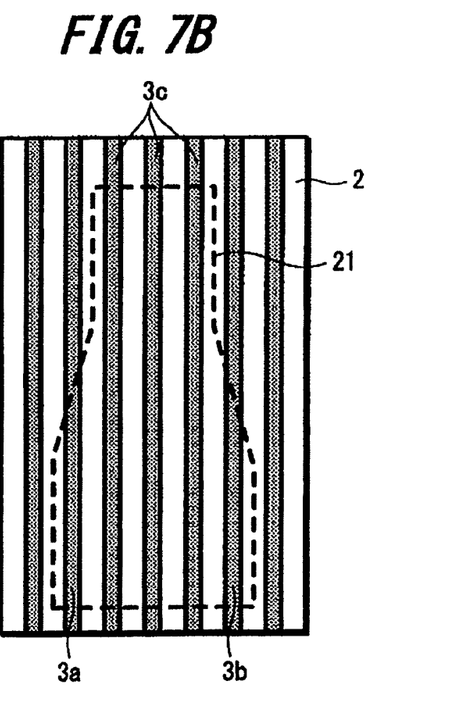
FIG. 7B is an illustration of electrodes arranged in a plate-shaped body to be molded into a tubular body whose diameter varies stepwise.

In the case of forming a tubular body having different outside diameters at opposite ends as shown in FIG. 7B, the cutting can be conducted so that three electrodes are included in the plate-shaped body in the development shape as indicated by broken line 21 in FIG. 7B.

It should be noted here, however, that in the plate-shaped body indicated by broken line 21 in FIG. 7B, three electrodes are arranged at an end portion on the side of smaller diameter after press working, whereas five electrodes are arranged at an end portion on the larger diameter side.

In the tubular body formed from the plate-shaped body with the shape shown in FIG. 7A, if blood sampled via the small diameter side end portion reaches electrodes 3a, 3b, these electrodes can be used for measurement of blood glucose level. For purposes of assuring proper blood sampling, however, it is preferable to select measuring and counter electrodes from among the electrodes 3c which extend up to the end portion on the small diameter side.

Such a configuration in which three or more electrodes are arranged in the plate-shaped body helps ensure that even if one of the electrodes is damaged during press working or welding, the remaining electrodes can be put to use as a working electrode and a counter electrode.

Figure 8A:
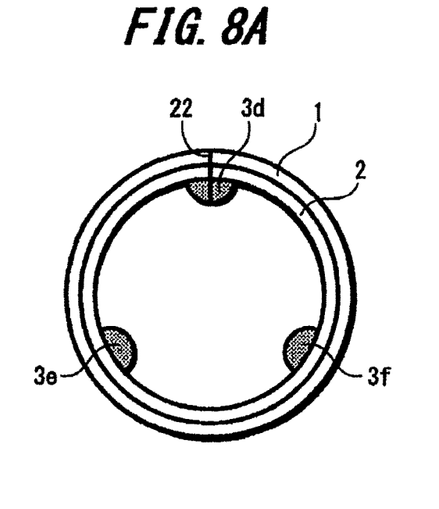
FIG. 8A is an illustration of a case in which one of electrodes is located on a joint surface of a tubular body.

For instance, in FIG. 8A, three electrodes 3d, 3e, 3f are provided on the inner wall surface of the tubular body 1, with the insulation layer 2 between the electrodes and the tubular body. The electrode 3d arranged near a joint surface 22 joined by press working or welding may have been damaged by the welding heat. In such a case, by using the electrodes 3e and 3f as a working electrode and a counter electrode, current can be measured rather assuredly.

Figure 8B:
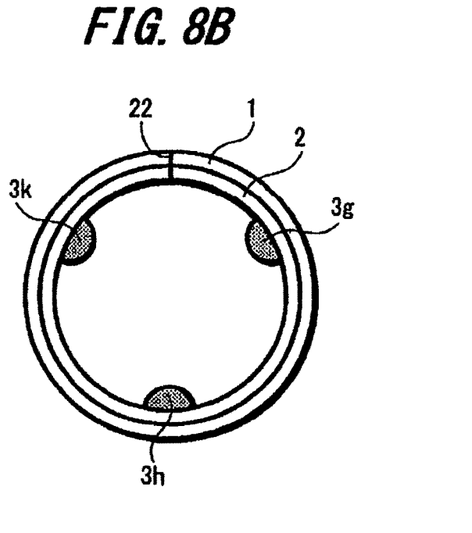
FIG. 8B is an illustration of a case in which one of electrodes is located on an inner wall surface of a tubular body at a position opposite to a joint surface of the tubular body.

In FIG. 8B, an electrode 3h is located at a position opposite to the joint surface 22. The electrode formed in this position may have been damaged under a pressure exerted from the upper die 15 (see FIG. 5B) during press working.

In this case, therefore, by using electrodes 3g, 3k as a working electrode and a counter electrode, it is possible to avoid generating an error in the measured value of current.

Figure 9A:
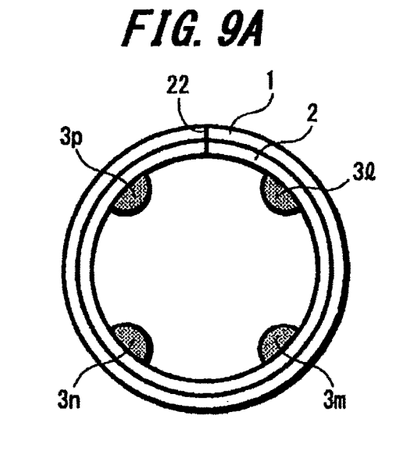
FIG. 9A is an illustration of a case in which four electrodes are disposed in a tubular body.
Figure 9B:
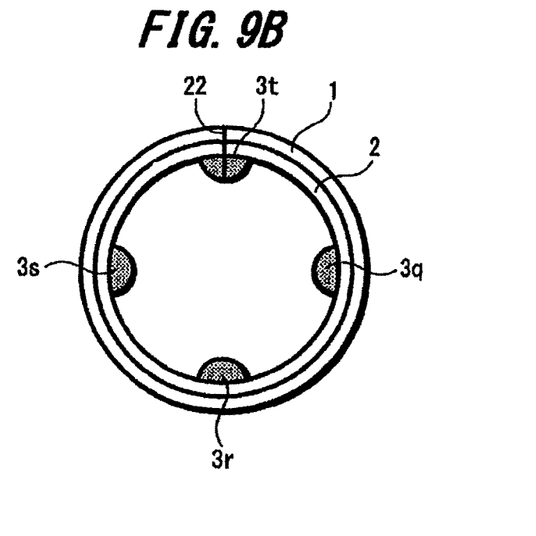
FIG. 9B is an illustration of a condition in which, of four electrodes disposed in a tubular body, two are located at parts which may be damaged.

Further, FIGS. 9A and 9B show cases where four electrodes are arranged in the tubular body 1, with the insulation layer 2 between the tubular body and the electrodes.

In FIG. 9A, four electrodes 3l, 3m, 3n, 3p are arranged inside the tubular body 1. The positions at which the electrodes are located are deviated from the joint surface 22 of the tubular body 1 and from that position on the inner wall surface of the tubular body 1 which is opposite to the joint surface 22.

In this case, therefore, none of the electrodes 3l, 3m, 3n, 3p is likely to be damaged. An arbitrary two of the electrodes can be selected for use as a working electrode and a counter electrode.

On the other hand, in FIG. 9B, of the four electrodes 3q, 3r, 3s, 3t, the electrode 3t is located near the joint surface 22 of the tubular body 1, and the electrode 3r is located at that position on the inner wall surface of the tubular body 1 which is opposite to the joint surface 22.

The electrode 3t may have been damaged during welding of the joint surface 22. The electrode 3r may have been damaged under the pressure exerted during press working.

In this case, therefore, by selecting the electrodes 3q, 3s for use as a working electrode and a counter electrode, a current can be measured in an assured manner.

Thus, by arranging three or more electrodes in the tubular body at regular intervals (i.e., at evenly spaced apart intervals or equal angular spacing), it is possible to obviate a situation in which a damaged electrode might be used as a working electrode or a counter electrode.

It has been found that the parts where an electrode may be damaged are two positions, one of which is a position near the joint surface of the tubular body and the other of which is a position, opposite to the joint surface of the tubular body, on the inner wall surface of the tubular body. Accordingly, when four or more electrodes are arranged in one plate-shaped body at regular intervals, two or more electrodes are necessarily present in the state of being free of damage, so that these electrodes can be put to use as a working electrode and a counter electrode.

Besides, in the case where the electrodes are arranged at regular intervals as shown in FIG. 7, it is possible to leave, without fail, not less than a predetermined number of electrodes on the plate-shaped body, even if the plate-shaped body is cut at random without performing any position adjustment.

Therefore, it is preferable to form electrodes at regular intervals by setting an inter-electrode distance so that three or more electrodes are left in the plate-shaped body. Accordingly, by cutting the plate-shaped body at random in a direction orthogonal to the longitudinal axis thereof, it is ensured that even an electrode is arranged near the joint surface of the tubular body or at a position where a pressure is exerted during press working and is damaged, the remaining electrodes can be put to use as a working electrode and a counter electrode.

In other words, a positioning process can be omitted at the time of cutting, so that enhanced productivity is promised and the manufacturing cost can be lowered.

2. Second Embodiment
2-1. Constituent Measuring Device

As a second embodiment, an example of a configuration of a constituent measuring device for measurement of blood glucose level by use of the above-described tubular sensor 100 will be described.

FIG. 10 is a schematic block diagram showing a configuration of a constituent measuring device 200 according to the second embodiment. The constituent measuring device 200 according to this embodiment includes, for example, a blood sampling chip 30 configured to sample blood and generate an electrical signal according to the amount of glucose in the blood thus sampled, and a measuring unit 60 configured to measure the electrical signal generated in the blood sampling chip 30.

In addition, the constituent measuring device 200 according to this embodiment further includes a control unit 70 configured to compute a detection signal obtained upon measurement by the measuring unit 60 and determine the blood glucose level of the blood sampled, and a display unit 80 configured to display the blood glucose level computed in the control unit 70.

The blood sampling chip 30 includes a puncture needle unit 40, and a housing 50 for holding the puncture needle unit 40. The housing 50 is provided with an internal cavity 51 extending throughout the longitudinal extent of the housing, with the puncture needle unit 40 held in the cavity.

The puncture needle unit 40 includes the tubular sensor 100 disposed at a distal end of the unit, a hub 41 for holding the tubular sensor 100, a gripped section 42 connected and secured to a rear stage of the hub 41, and a pair of wires 45.

This tubular sensor 100 is the one which has been shown in the first embodiment (see FIG. 1), and the inside diameter of a distal portion thereof is so small that blood can be guided into the tubular sensor 100 by capillary action. In addition, the tubular sensor 100 has its rear end portion held in the hub 41.

Besides, the gripped section 42 is connected and secured to the rear stage of the hub 41, and the tubular sensor 100 and the gripped section 42 are in contact with each other in the cavity in the hub 41.

In addition, the cavity in the tubular sensor 100 communicates rearward through a vent hole 42a and a central hole 42b provided in the gripped section 42.

Besides, the gripped section 42 is gripped by a gripping section 43. An urging bar 44 disposed inside the gripping section 43 urges the puncture needle unit 40 through the gripping section 43 by urging means (not shown). As a result, the cutting edge surface of the tubular sensor 100 is moved into and out of the housing 50.

The electrodes in the tubular sensor 100 are connected to the wires 45. The wires 45 are so set, for example, as to pass through the vent hole 42a of the gripped section 42, and thereafter penetrate to an outer surface of the gripped section 42, whereon they are extended on the outer surface of the gripped section 42.

On the other hand, on an inner surface of the gripping section 43 for gripping the gripped section 42, a pair of terminal wires 46 which make contact with the wires 45 are provided. The terminal wires 46 are connected to the measuring unit 60 configured to measure the signal from the tubular sensor 100.

The measuring unit 60 includes a power supply 63, a voltage changing circuit 61 configured to change a voltage supplied from the power supply 63 and impress the thus changed voltage on the electrodes of the tubular sensor 100, and a current measuring section 62 configured to measure a current generated according to the amount of a constituent in a liquid sampled into the tubular sensor 100.

A predetermined voltage is impressed between the electrodes in the tubular sensor 100 by the voltage changing circuit 61, whereby a current according to the amount of glucose in blood is made to flow through the current measuring section. The change in the current is measured by the current measuring section 62, which outputs a detection signal to the control unit 70.

The control unit 70 computes blood glucose level by a computation treatment based on the detection signal inputted thereto and while performing, if required, a corrective computation. The blood glucose level thus computed is outputted to and displayed on the display unit 80, for example.

Thus, in the constituent measuring device 200 according to this embodiment, the tubular sensor 100 shown in the first embodiment is used. In the tubular sensor 100, the electrodes are secured to the inner wall surface thereof, so that the inter-electrode distance is securely kept at a constant value. Accordingly, measurement of blood glucose level, for example, can be performed with high accuracy.

In measuring a patient's blood glucose level, first, the patient's skin is instantaneously punctured by the tubular sensor 100. Next, while using the tubular sensor 100 as it is, blood is sampled into the tubular sensor 100 from a minute blood lump 90 generated in the cavity 51, whereby measurement of the blood glucose level can be performed. In other words, the blood glucose level measurement can be carried out by a highly simplified operation. Consequently, the burden on the patient can be lightened.

In addition, the blood glucose level measurement can be carried out by use of only the blood sampled into the tubular sensor 100. Therefore, the amount of blood necessary for the measurement can be made small. Especially, in the case where use is made of the tubular body 1 having different diameters at one end and the other end thereof, the blood sampled via the smaller diameter part side would not easily enter a larger diameter part side due to capillarity. This helps achieve a further reduction in the amount of blood to be sampled.

When a reagent is placed only in the smaller diameter part on the distal side of the tubular sensor 100, a further reduction in the amount of blood to be sampled can be achieved, which naturally is preferable. The insulation layer 2 formed on the inner wall surface of the tubular sensor 100 is formed of a plastic material and, therefore, is hydrophobic. On the other hand, the reagent is hydrophilic. Therefore, blood is sampled only into a region where the reagent is applied. Accordingly, the measurement can be performed by use of only the blood sampled into the smaller diameter part coated with the reagent, for example. Consequently, the amount of blood to be sampled can be reduced more assuredly.

While an example of measuring blood glucose level in blood has been shown here, the tubular sensor according to the present invention can be used, for example, as a sensor for measuring the sugar content of a fruit or vegetable, or as a sensor for measuring a chemical constituent of river water or industrial liquid waste.

Embodiments of the tubular sensor, the constituent measuring device, and the tubular sensor manufacturing method disclosed here have been described above. The invention is not limited, however, to the precise embodiments and variations described. Various changes, modifications and equivalents could be effected or carried out by one skilled in the art without departing from the spirit and scope of the invention as defined in the appended claims. It is expressly intended that all such changes, modifications and equivalents which fall within the scope of the claims are embraced by the claims.

What is claimed is:

1. A puncture needle manufacturing method comprising:
   forming an insulation layer and a plurality of spaced apart elongated electrodes on a metal sheet so that the electrodes overlie the insulation layer;
   cutting the metal sheet, the insulation layer, and a portion of the electrodes on the metal sheet to form a plate-shaped body, the plate-shaped body possessing a proximal end, a distal end, and a middle portion, the plate-shaped body having a width at the proximal end greater than a width at the distal end, and the middle portion of the plate-shaped body tapering in width towards the distal end;
   press-working the plate-shaped body to form the plate-shaped body into a tubular body, the tubular body possessing an outer diameter at a distal end greater than an outer diameter at a proximal end; and
   forming a pointed, beveled end portion at the distal end of the tubular body, wherein the press-worked tubular body possesses a distal portion and a proximal portion, the tubular body comprising:
   a distal plurality of separate and circumferentially spaced apart electrodes fixed on the insulation layer in the distal portion of the tubular body;
   a proximal plurality of separate and circumferentially spaced apart electrodes fixed on the insulation layer in the proximal portion of the tubular body; and
   the distal plurality of electrodes being a different number of electrodes than the proximal plurality of electrodes.

2. The puncture needle manufacturing method according to claim 1, wherein
   the tubular body comprises a longitudinally extending seam at which opposite edges of the tubular body face one another; and
   the method further comprises welding a longitudinally extending seam of the tubular body after the press-working of the plate-shaped body.

3. The puncture needle manufacturing method according to claim 1, wherein the cutting of the metal sheet comprises cutting the metal sheet so that the plate-shaped body remains partially connected, during at least some of the press-working, to a frame part of the metal sheet.

4. The puncture needle manufacturing method according to claim 1, wherein the plurality of electrodes are positioned in the tubular body at equally spaced intervals.

5. The puncture needle manufacturing method according to claim 1, wherein the plate-shaped body includes at least three spaced-apart electrodes.

* * * * *